US00PP13737P3

(12) United States Plant Patent
Zipperer, III

(10) Patent No.: US PP13,737 P3
(45) Date of Patent: Apr. 29, 2003

(54) GLADIOLUS PLANT NAMED 'ROSIEBEE RED'

(76) Inventor: John O. Zipperer, III, Urbanization Campo Alegre, #99 El Gorrion, Quito (EC)

( * ) Notice: Subject to any disclaimer, the term of this patent is extended or adjusted under 35 U.S.C. 154(b) by 0 days.

(21) Appl. No.: 09/742,726

(22) Filed: Dec. 20, 2000

(65) Prior Publication Data

US 2002/0002720 P1 Jan. 3, 2002

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/877,571, Zipperer, III, filed Jun. 8, 2001.
U.S. patent application Ser. No. 09/877,572, Zipperer, III, filed Jun. 8, 2001.
U.S. patent application Ser. No. 09/877,573, Zipperer, III, filed Jun. 8, 2001.
U.S. patent application Ser. No. 09/877,574, Zipperer, III, filed Jun. 8, 2001.
U.S. patent application Ser. No. 09/877,575, Zipperer, III, filed Jun. 8, 2001.
U.S. patent application Ser. No. 09/918,662, Zipperer, III, filed Jul. 31, 2001.
U.S. patent application Ser. No. 09/918,660, Zipperer, III, filed Jul. 31, 2001.
U.S. patent application Ser. No. 09/918,663, Zipperer, III, filed Jul. 31, 2001.

*Primary Examiner*—Bruce R. Campell
*Assistant Examiner*—Annette H. Para
(74) *Attorney, Agent, or Firm*—Laura G. Barrow

(57) ABSTRACT

A new and distinct gladiolus cultivar, designated 'Rosiebee Red', is shown and described. Compared to the 'Advance' variety, the 'Rosiebee Red' cultivar has a larger bloom size about one to two fewer flowers per spike, and is able to maintain on the spike about four to five more flowers in open bloom.

4 Drawing Sheets

The present invention comprises a new and distinct cultivar of a *Gladiolus l.* referred to by the cultivar name 'Rosiebee Red'.

BRIEF DESCRIPTION OF THE PHOTOGRAPHS

ASEXUAL REPRODUCTION

The new cultivar was originated by the Applicant in a controlled proprietary breeding program in Ft. Myers, Fla. wherein selected gladiolus varieties were crossed. The female parent was an unpatented coral color gladiolus variety named 'T-103', having a length near 140 cm, a short head having about 16 florets, and a thick and heavy stem. The male parent was an unpatented red gladiolus variety named 'Advance', having a length of about 140 cm, floppy wide leaves, a heavy stem, and about 17–18 florets per stem. The seeds were planted in Ft. Myers, Fla., and the selection of the 'Rosiebee Red' cultivar was made in spring 1988. Asexual reproduction of the 'Rosiebee Red' cultivar was achieved in Ft. Myers, Fla. by collecting cormels from the first corm. All subsequent asexual reproductions of the 'Rosiebee Red' are true to the original variety.

BOTANICAL DESCRIPTION

Figure 1:
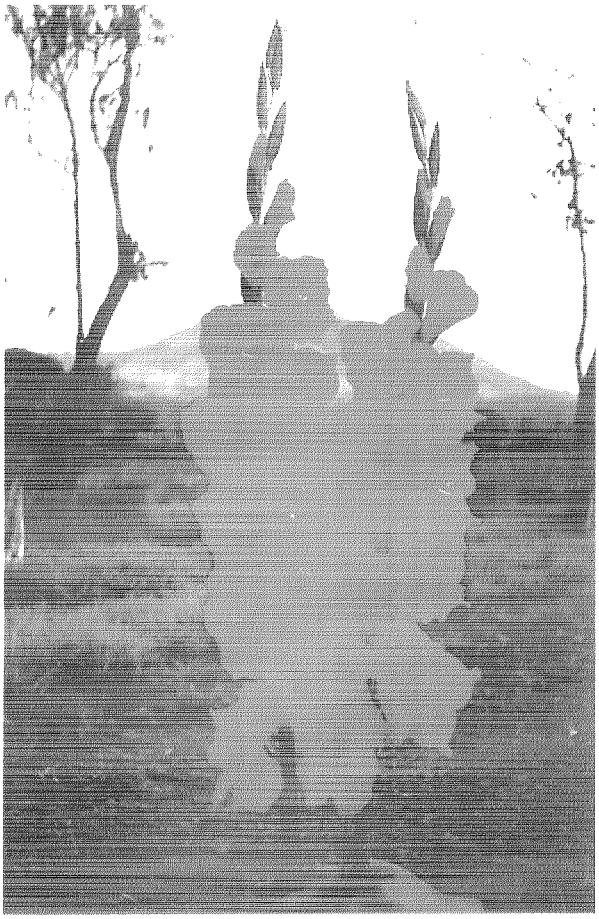
FIG. 1 is a photograph of two 'Rosiebee Red' cultivar plants in bloom.

The accompanying color photograph (FIG. 1) shows the inflorescence and various stages of blooming of two 'Rosiebee Red' cultivar plants.

The following botanical description of the 'Rosiebee Red' cultivar was observed when the plant was 75 days old grown under the following conditions:

1. Twelve-hour daylight days with high light intensity;
2. Temperatures: 58–60° F. (low's) and 69–75° F (high's);
3. Humidity: 50–55%
4. Rainfall: 2–3 inches/month.

All color descriptions with respect to parts of the cultivar where color is a distinguishing feature, are made to The Royal Horticultural Society Colour Chart, except where terms of ordinary usage and dictionary meaning are used.

Figure 4:
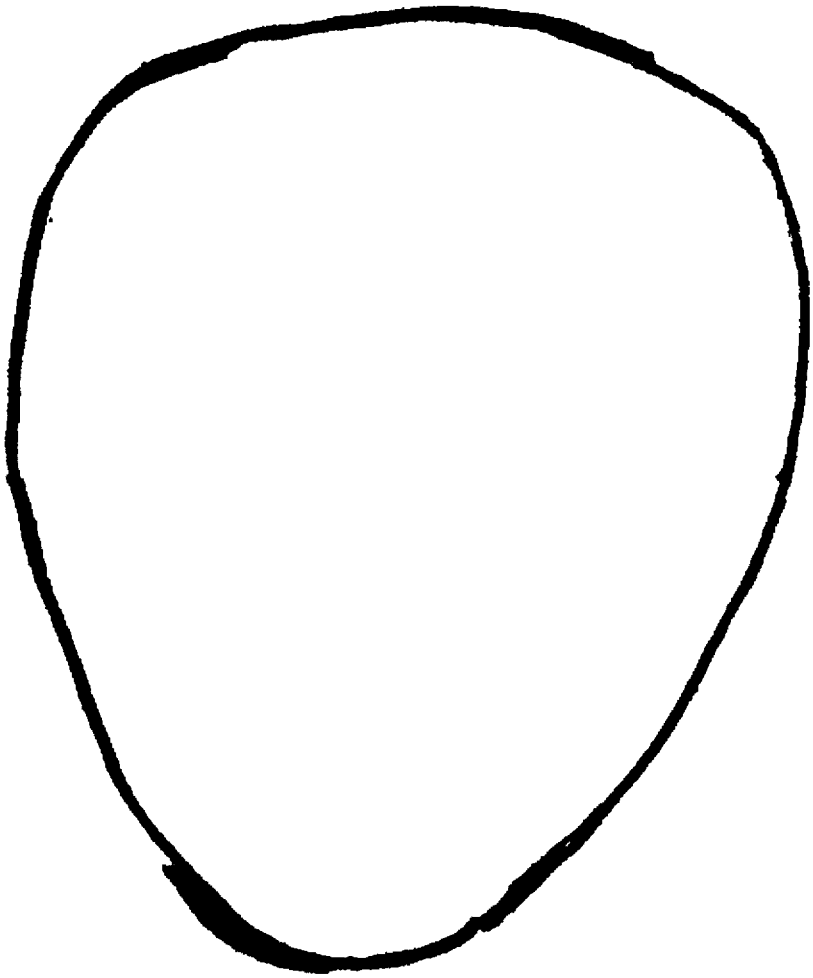
FIG. 4 is a drawing illustrating the shape of the petals.

The bud size of the 'Rosiebee Red' cultivar, when first showing color, is 7 cm in length. The flowers of the 'Rosiebee Red' cultivar each comprise five large petals and one small petal at the bottom of the corolla. All of the petals of the corolla are present in an overlapping arrangement. Each petal has crease running up its middle. The shape of the petal is illustrated best in FIG. 4, with dimensions of 2–2.5 inches in length and 2 inches in width (at the widest point then tapering down as shown). The flowers of the 'Rosiebee Red' cultivar are arranged on the spike of the plant on one side in a tight, overlapping zig-zag.

The corolla color of the deep portion of the flower's throat is dark red with the petals having a uniformly red color ɔre specifically, the color of the tight bloom and in open rfect condition is Red Group 44B. The color of the bloom en going down is Red Group 44C. The pistils of the flower : white (White 155D) with a red stem color (Red 43D). e stamens are white 155A with a red stem (Red 43). The ımeter of the bloom is about 13 cm.

Figure 2:
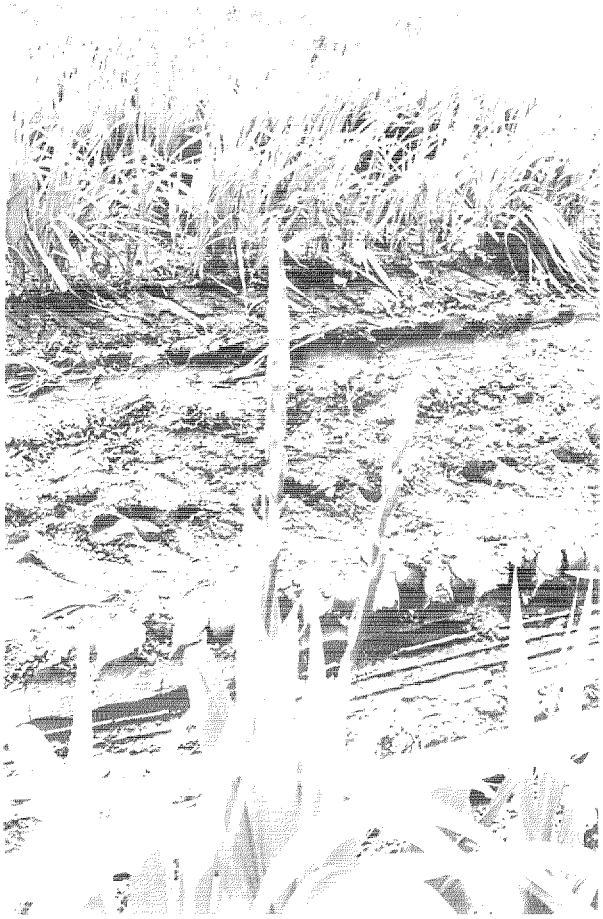
FIG. 2 is a photograph of two 'Rosiebee Red' cultivar plants prior to blooming.

The spike has a green color tinged with red (Greyed Red oup 178B) (FIG. 2). Various factors will affect spike ıgth, however, including temperature (larger spikes occur cooler weather), irrigation, light intensity, fertilization, l type (larger spikes occur in heavy soils versus sandy l), and bulb size (larger bulbs result in larger spikes). The :sent 'Rosiebee Red' cultivar is typically very long (about 0 cm) and heavy when grown in fine silt soil in Ecuador, ıerein the day-lengths are twelve hours and temperatures : 75–76° F. (high) and 58–62° F. (low).

Figure 3:
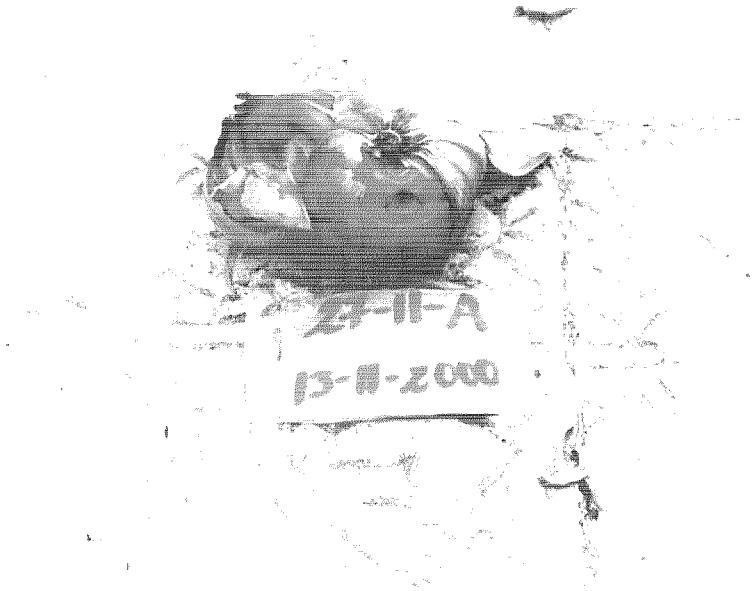
FIG. 3 is a photograph of a corm of the 'Rosiebee Red' cultivar.

The corms of the 'Rosiebee Red' cultivar are a typical ıpe for the gladiolus and have an orange/yellow color der the husk (FIG. 3).

The leaves of the 'Rosiebee Red' cultivar are wide, each ıering to a point with parallel veins running the length of : leaf. The leaf dimensions of cultivars grown from jumbo lbs are typically 87 cm×4.5–5.5 cm.

GENERAL OBSERVATIONS

Compared to the gladiolus variety 'Advance,' the 'Rosi-ɜe Red' cultivar has a larger bloom size, about one to two fewer flowers per spike, and is able to maintain on the spike about four to five more flowers in open bloom. Another distinguishing feature of the 'Rosiebee Red' cultivar is that can hold eight to ten flowers in open bloom, beginning with a tight cut stem.

Disease tolerance for the 'Rosiebee Red' cultivar is similar to the 'Advance' variety. Red spiders and worms are attracted to the 'Rosiebee Red' cultivar similar to the 'Advance' variety and other red gladiolus varieties. The 'Rosiebee Red' grows well all year long in south Florida.

The 'Rosiebee Red' cultivar does not emit a fragrance.

The flowers of the 'Rosiebee Red' cultivar will bloom under long and short day lengths, having been tested down to 10.5 hours of day length in south Florida. The flowers open fast in the field; however, the cut stems may be shipped for up to a week prior to blooming. Performance under hot conditions and under winter conditions in south Florida has been good.

I claim:

1. A new and distinct gladiolus plant, cultivar 'Rosiebee Red', as shown and described herein.

* * * * *

UNITED STATES PATENT AND TRADEMARK OFFICE

CERTIFICATE OF CORRECTION

PATENT NO. : PP 13,737 P3
DATED : April 29, 2003
INVENTOR(S) : John O. Zipperer, III It is certified that error appears in the above-identified patent and that said Letters Patent is hereby corrected as shown below:

Title page,
Item [30], Foreign Application Priority Data, insert the following:
-- EP2000/0889 - June 9, 2000 --

Column 1,
Lines 1-3, replace with the following recitation:
-- Botanical classification: Gladiolus L.
Variety denomination: 'Rosiebee Red'

Column 2,
Line 8, after "conditions" add -- in Eduador --
Line 18, add the following:

-- Color observations with respect to the RHS Colour Chart were made in the Netherlands under similar environmental conditions as described above, but at increased day lengths of 12 to 17 hours and 50% to 65% humidity.

The present 'Rosiebee Red' cultivar is typically very long (about 140 cm) and heavy when grown in fine silt soil in Ecuador, wherein the day-lengths are twelve hours and temperatures are 75-76 °F (high) and 58-62 °F (low). Various factors will affect spike length, however, including temperature (larger spikes occur in cooler weather), irrigation, light intensity, fertilization, soil type (larger spikes occur in heavy soils versus sandy soil), and bulb size (larger bulbs result in larger spikes).

The spike is Greyed Red Group 178B on the back side of the stem between the flower buds (Fig. 2). The leaves of the 'Rosiebee Red' cultivar are wide, each tapering to a point with parallel veins running the length of the leaf. The leaf dimensions of cultivars grown from jumbo bulbs are typically 87 cm X 4.5-5.5 cm. The leaf color, on both sides, is Green Group 137C. The leaves have a tendency to lay over versus being upright, which gives them a floppy appearance. --

Column 3,
Line 3, after "Red Group 44C.", delete "The pistils of the flower" and
Lines 4-6, replace with the following:

-- The color of the pistil stem is White Group N155D. The color of the pistil head is Red Group 43D on the exterior and White Group N155D on the tips. The stamen head color is White Group 155D, with the color of the top of the stamen stem being Red Group 42C and the rest of the stamen stem being White Group N155A. The diameter of the bloom is about 13 cm grown under conditions in Ecuador. --

Lines 7-16, delete lines.
Lines 18-19, replace with the following: -- shape for the gladiolus. The color under the husk on the top of the bulb one day after harvest is Red Group 40D (Fig.3). --
Lines 20-23, delete lines.
Line 28, after "bloom", insert -- that is about 1 cm larger in diameter --

UNITED STATES PATENT AND TRADEMARK OFFICE

CERTIFICATE OF CORRECTION

PATENT NO. : PP 13,737 P3
DATED : April 29, 2003
INVENTOR(S) : John O. Zipperer, III It is certified that error appears in the above-identified patent and that said Letters Patent is hereby corrected as shown below:

Column 4,
Line 2, after "bloom" insert -- and is able to withstand high summer temperatures without burning the florets. This is a significant improvement over the 'Advance' variety, which on the contrary burns easily at higher temperatures. --
Line 8, after "variety." insert the following text: -- Both varieties are more susceptible to Curvalaria than usual due to the presence of wide floppy foliage which stays wet longer than upright foliage. --
Line 10, delete "The" and delete line 11.
Lines 18-21, replace with the following text:

-- open fast in the field. Stems harvested with one bloom showing color have been packed in a shipping box and placed in a refrigerated room at 36 °F for a week to simulate the time a flower could be in a box until used by the retail florist. The stems are then placed in water to check opening ability of the cultivar. The 'Rosiebee Red' cultivar had no problems opening. --

Signed and Sealed this

Twenty-fourth Day of August, 2004

JON W. DUDAS
*Director of the United States Patent and Trademark Office*